United States Patent [19]

Goto et al.

[11] Patent Number: 4,782,183

[45] Date of Patent: Nov. 1, 1988

[54] METHOD FOR MANUFACTURE OF AMINO-CARBOXYLIC ACID SALTS

[75] Inventors: Takakiyo Goto; Hiromi Yokoyama, both of Yokohama; Hideyuki Nishibayashi, Machida, all of Japan

[73] Assignee: Nippon Shokubai Kagaku Kogyo Co., Ltd., Japan

[21] Appl. No.: 863,718

[22] Filed: May 16, 1986

Related U.S. Application Data

[63] Continuation of Ser. No. 656,969, Oct. 2, 1984, abandoned.

[30] Foreign Application Priority Data

| Oct. 5, 1983 | [JP] | Japan | 58-185179 |
| Oct. 6, 1983 | [JP] | Japan | 58-185874 |
| Nov. 1, 1983 | [JP] | Japan | 58-203650 |
| Nov. 8, 1983 | [JP] | Japan | 58-208246 |

[51] Int. Cl.[4] .................... C07C 51/00; C07C 51/097
[52] U.S. Cl. .................................. 562/526; 562/539; 562/553; 562/571; 562/572
[58] Field of Search ............ 562/539, 572, 571, 553, 562/526; 260/413

[56] References Cited

U.S. PATENT DOCUMENTS

| 1,977,750 | 10/1934 | Young . | |
| 2,384,817 | 9/1945 | Chitwood | 562/539 |
| 2,746,993 | 5/1956 | Dean . | |
| 3,535,373 | 10/1970 | Jackisch . | |
| 3,535,374 | 10/1970 | Jackisch . | |
| 3,535,375 | 10/1970 | Jackisch . | |
| 3,578,709 | 5/1971 | Bishop et al. . | |
| 3,739,021 | 6/1973 | Peppel et al. . | |
| 3,833,650 | 9/1974 | Schulze et al. . | |
| 3,842,081 | 10/1974 | Schulze et al. . | |
| 4,319,037 | 3/1982 | Yoneoka | 560/239 |

FOREIGN PATENT DOCUMENTS 51-65708  6/1976  Japan .................................. 560/239

OTHER PUBLICATIONS

J. Org. Chem., 3, 242 (1938) R. E. Dunbar.
Ind. Eng. Chem., 43, 1804 (1951) J. M. Church.
Nature, 179, 668 (1957) A. Bjelanski.

Primary Examiner—Werren B. Lone
Attorney, Agent, or Firm—Omri M. Behr

[57] ABSTRACT

A method for the manufacture of an aminocarboxylic acid salt which comprises subjecting to dehydrogenation an amino alcohol represented by the general formula (I):

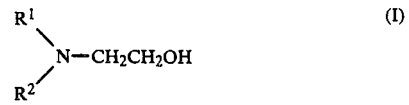

(I)

wherein $R^1$ and $R^2$ denote hydrogen, —$CH_2CH_2OH$, an alkyl group having 1 to 18 carbon atoms or an aminoalkyl group having 2 or 3 carbon atoms, which may be the same or different, in the presence of the hydroxide of at least one metal selected from the group consisting of alkali metals and alkaline earth metals, water and a catalyst containing copper metals or a copper compound and a zirconium compound.

17 Claims, No Drawings

METHOD FOR MANUFACTURE OF AMINO-CARBOXYLIC ACID SALTS

This application is a continuation of application Ser. No. 656,969, filed Oct. 2, 1984, abandoned.

BACKGROUND OF THE INVENTION

1. Field of the Invention

This invention relates to aminocarboxylic acid salts. More particularly, this invention relates to a method for the manufacture of aminocarboxylic acid salts by the reaction of amino alcohols in the presence of an alkali metal compound.

2. Description of Prior Art

Aminocarboxylic acid salts find utility in various applications. The glycine salt, for example, is generally neutralized into glycine and, as such, is widely used as an additive in processed meat, refreshing beverage, instant food and other processed foodstuffs. It is also used widely as raw material for pharmaceuticals, agricultural chemicals and pesticides and amino acids. The iminodiacetic acid salt is generally neutralized into iminodiacetic acid and is used in various applications utilizing the action of chelation and is also used as raw material for agricultural chemicals and pharmaceuticals. The nitrilotriacetic acid salt, because of its outstanding chelating ability, is extensively used in water-softening agent, scouring aid, dyeing assistant, paper-coating agent, scale inhibitor, detergent builder and agent for preventing soap from degeneration.

For commercial production of such aminocarboxylic acid salts, the Strecker Process which uses hydrogen cyanide and formaldehyde as principal raw materials is generally known. Since hydrogen cyanide is violently toxic, the equipment for production, the handling of raw materials and the selection of site for plant, etc. are strictly restricted. Since the majority of the hydrogen cyanide is obtained as a by-product in the manufacture of acrylonitrile, the hydrogen cyanide causes a serious problem about the steady acquisition of raw material.

It has been known to the art to produce aminocarboxylic acid salt by oxidative dehydrogenation of amino alcohol in the presence of an alkali hydroxide (U.S. Pat. Nos. 2,384,816. 2,384,817. 3,535,373. 3,842,081 and 3,739,012). For example, U.S. Pat. No. 2,384,816 discloses a method for effecting the production of glycine salt by the reaction of monoethanolamine with alkali metal hydroxides in the absence of catalyst. This method has a disadvantage that the reaction consumes much time and glycine salt is obtained in low yields. U.S. Pat. No. 2,384,817 discloses a method involving the reaction of monoethanolamine with potassium hydroxide at elevated temperatures in the form of flakes in the presence of a copper catalyst in the absence of water. But it does not disclose the yield of glycine salt. The same patent discloses a method for the reaction of monoethanolamine with potassium hydroxide in the presence of cadmium oxide which is poisonous under the same conditions, but the yield of glycine salt is low. Further, U.S. Pat. No. 3,842,081 discloses a method for producing an iminodiacetic acid salt by the reaction of diethanolamine with sodium hydroxide in the presence of a cadmium oxide catalyst. This method gives the product at realtively high yields. U.S. Pat. Nos. 3,535,373. 3,578,709 and 3,739,021 disclose a method for producing nitrilotriacetic acid salt by the reaction of triethanolamine with alkali metal hydroxides in the presence of a cadmium oxide catalyst. This method gives the product in rather high yields. Then, U.S. Pat. No. 3,578,079 discloses a method for the reaction of triethanolamine with alkali metal hydroxides in the presence of a zinc oxide catalyst. This method does not give the product in satisfactory yields.

The conventional methods are such that the reactions using no catalyst and the reactions using zinc oxide as a catalyst give their products in very low yields. Further, the methods which use a cadmium oxide catalyst have a possibility that the cadmium compound which is toxic will contaminate the reaction product and, by reason of this possibility, cannot be adopted where the use found for the reaction product does not tolerate the presence of the cadmium compound. Moreover, the plant effluent entraining the cadmium compound flows into a nearby river and lake, it will raise a serious social problem. On the other hand, U.S. Pat. No. 2,284,817 does not disclose the reaction in the presence of water, when copper is used as the catalyst. U.S. Pat. No. 2,384,818 shows that the reation of monoethanolamine in the absence of water gives low yield.

An object of this invention, therfore, is to provide a novel method for the manufacture of an aminocarboxylic acid salt.

Another object of this invention is to provide a method for the manufacture of an aminocarboxylic acid salt by the dehydrogenation of an amino alcohol in the presence of an alkali metal compound without involving use of a cadmium compound which is dangerous because of toxicity.

SUMMARY OF THE INVENTION

The objects described above are accomplished by a method for the manufacture of an aminocaroxylic acid salt which comprises subjecting to dehydrogenation of an amino alcohol represented by the general formula I:

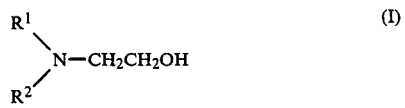

wherein $R^1$ and $R^2$ denote hydrogen, $-CH_2CH_2OH$, an alkyl group having 1 to 18 carbon atoms or an aminoalkyl group having 2 or 3 carbon atoms, which may be the same or different, in the presence of a hydroxide of at least one metal selected from the group consisting of alkali metals and alkaline earth metals, water and a catalyst containing copper or copper and zirconium compound.

In accordance with this invention, owing to the use of the aforementioned catalyst, the aminocarboxylic acid salt aimed at can be produced in very high yields more quickly under milder reaction conditions than the conventional methods. Thus, the method allows a notable reduction in the production cost of aminocarboxylic acid salts and permits easy commercialization of the manufacture of aminocaroxylic acid salts from amino alcohols.

DESCRIPTION OF PREFERRED EMBODIMENTS

In accordance with this invention, the dehydrogenation of an amino alcohol represented by the aforementioned general formula I in the presence of the hydroxide of at least one metal selected from the group consisting of alkali metals and alkaline earth metals, water, and a catalyst containing copper or copper and zirconium compound produces a corresponding aminocarboxylic acid salt.

In the aforementioned general formula I, $R^1$ and $R^2$ denote hydrogen, $-CH_2CH_2OH$, an alkyl group having 1 to 18 or an aminoalkyl group having 2 or 3 carbon atoms which can be the same or different, and preferably denote hydrogen or $-CH_2CH_2OH$.

Typical amino alcohols are monoethanolamine, diethanaolamine, triethanolamine, N-methylethanolamine, N-ethylethanolamine, N-isopropylethanolamine, N-butylethanolamine, N-nonylethanolamine, N-(2-aminoethyl)ethanolamine, N-(3-aminopropyl)ethoanolamine, N,N-dimethylethanolamine, N,N-diethylethanolamine, N,N-dibutyl ethanolamine, N-methyl diethanolamine, N-ethyl diethanolamine, N-isopropyl diethanolamine, N-butyl diethanolamine, N-ethyl,N-(2-aminoethyl) ethanolamine, N-methyl,N-(3-aminopropyl) ethanolamine and the like.

The catalyst contains copper or copper and zirconium compound as an essential component. The copper as the catalyst is used in the form of metal or a copper compound. As the starting material for this copper, there may be used metallic copper, such inorganic salts as nitrate, sulfate, carbonate, oxides, halides and hydroxide, and such organic salts as formate, acetate, propionate, citrate and lactate. The form of the catalyst is not specifically limited. For example, a catalyst obtained by oxidizing the surface of metallic copper with air, oxygen or some suitable oxidizing agent and subsequently reducing the oxdized copper in an atmosphere of hydrogen gas, a catalyst obtained by developing Raney copper with an alkali and subsequently washing the developed Raney copper with water, a catalyst obtained by thermally decomposed copper formate, copper carbonate or some other copper salt, and other catalysts obtained by similarly activated copper in some way or other can be used advantageously. The copper catalyst thus obtained can be used directly or as deposited on an alkali resistant carrier.

In the copper and zirconium compound-containing catalyst, copper is used as metal or metal compounds, and zirconium is used as zirconium compounds. As the starting materials, there may be used inorganic salts such as nitrates, sulfates, carbonates, oxides halides and hydroxides, and organic salts such as formates, acetates, propionates, citrates, and lactates. Typical zirconium compounds are zirconium oxynitrate, zirconium nitrate, zirconium oxysulfate, zirxonium sulfate, zirconium oxycarbonate, zirconium carbonate, zirconium oxide, zirconium oxychloride, zirconium tetrachloride, zirconium hydroxide, zirconium oxyacetate, zirconium acetate, zirconium oxalate and the like. The form of this catalyst is not specifically limited. For example, a catalyst containing copper and zirconium compound which is obtained by dissolving a copper compound and a zirconium compound in water, adding an aqueous alkali solution to the resultant aqueous solution thereby causing percipitation of hydroxides, separating, washing with water, and drying the precipitate, oxidizing the precipitate in air or in oxygen, and thereafter subjecting the oxidized precipitate to reduction in an atmosphere of hydrogen gas is advantageously used. Another catalyst having copper deposited on zirconium oxide which is obtained by impregnating zirconium oxide with an aqueous copper compound solution, drying the wet zirconium oxide composite, oxidizing this composite in air or on oxygen, and thereafter subjecting the oxidized composite to reduction in an atmosphere of hydrogen gas is also used advantageously. In the copper and zirconium-containing catalyst, the copper content is desired to be 3 to 50% by weight, preferably 5 to 35% by weight, based on the total amount of copper and zirconium.

The amount of aforementioned catalyst to be used is in the range of 1 to 70% by weight, preferably 5 to 30% by weight based on the amount of the amino alcohols. The catalyst can generally be repeatedly used in the reaction at a temperature of not more than 200° C. It may he used on the one-pass basis. Of the aforementioned catalysts, the copper and zirconium-containing catalyst has higher activity and can decrease the reaction temperature to 10° to 20° C. and further enjoys higher selectivity and heat resistance than the copper catalyst without containing zirconium compound. Therefore, this catalyst is effective for enhancing yield of aminocarboxylic acid salts, decreasing the reaction temperature and using the catalyst repeatedly for a long time.

In the present invention, the presence of water is inevitable. Heretofore, it has been held that water promotes the decomposition of amino groups, especially primary and secondary amino groups. In the reaction of the present invention using copper or copper and zirconium compound, the decomposition of any amino group almost does not occur in the presence of water. Conversely, the presence of water offers an advantage that the reaction of the amino alcohols with the hydroxide of an alkali metal and/or an alkaline earth metal is allowed to proceed in a homogeneous system and to increase reaction velocity. It is an indispensable requirement for the production of an aminoacarboxylic acid salt in high yields. Presence of water is effective especially for a manufacture of glycine salt from nomoethanolamine and of iminodiacetic acid salt from diethanolamine. The amount of water to be used in the reaction is required to exceed 10% by weight and desired to fall in the range of 50 to 500% by weight.

The hydroxides of alkali metals which are usable for this invention include lithium hydroxide, sodium hydroxide, potassium hydroxide, rubidium hydroxide and cesium hydroxide. The hydroxides of alkaline earth metals which are usable herein include magnesium hydroxide, calcium hydroxide and barium hydroxide. Among other hydroxides enumerated above, particularly sodium hydroxide and potasium hydroxide are used advantageously. The amount of the hydroxide of an alkali metal and/or alkaline earth metal to be used is required to be an equivalent amount and desired to fall in the range of 1.0 to 2.0 equivalent relative to the hydroxyl group of the amino alcohols to be used in the reaction. The hydroxide of alkali metal and/or alkaline earth metal can be used in any of the form of flakes, powder, pellets and aqueous solution thereof. Generally from the standpoint of ease of handling, it can be used advantageously in the form of aqueous solution.

This invention does not discriminate the amino alcohols to be used as the raw material by its purity. To preclude inclusion of foreign matter in the produced aminocarboxylic acid salts, the amino alcohols to be used is desired to have as high purity as possible. The purity is desired to exceed 96% by weight generally and 99% by weight preferably.

To prevent of thermal decomposition or hydrogenolysis of the C-N bond of the amino alcohols and the formed aminocarboxylic acid salts, the reaction temperature is not allowed to exceed 220° C. The reaction is carried out generally at a temperature in the range of 120° to 220° C., preferably 140° to 200° C. At temperatures exceeding 200° C., in case of the copper catalyst and exceeding 220° C. in case of the copper and zirconium compound containing catalyst the catalyst begins to sinter, lose surface area of the catalyst and suffers loss of catalytic activity. If the catalyst is desired to be used repeatedly, therefore, the reaction is preferably carried out at temperatures not exceeding 200° C. in case of using the copper catalyst and not exceeding 220° C. in case of using the copper and zirconium compound containing catalyst.

As concerns the reaction pressure, since the reaction is dehydrogenation, the reaction pressure is desired to be as low as possible to ensure high reaction velocity. Generally, it is required to exceed the minimum pressure at which the reaction proceeds in a liquid phase. It is desired to fall in the range of 0 to 30 kg/cm$^2$.G (gauge pressure), preferably in the range of 5 to 20 kg/cm$^2$. G.

The reaction may be carried out either batchwise on continuously.

The aminocarboxylic acid salts obtained by the reaction described above are which issue from the conversion of the hydroxyl group in the amino alcohols of the aforementioned general formula I to a corresponding carboxylic aicd salt.

Typical examples of the product of this reaction are glycine salt, iminodiacetic acid salt, nitrilotriacetic acid salt, N-methylglycine salt, N-ethylglycine salt, N-isopropylglycine salt, N-butylglycine salt, N-nonyl glycine salt, N-(2-aminoethyl)glycine salt, N-(3-aminopropyl)glycine salt, N,N-dimethylglycine salt, N,N-diethylglycine salt, N,N-dibutyl glycine salt, N-methyl iminodiacetic acid salt, N-ethyliminodiacetic acid salt, N-isopropyl iminodiacetic acid salt, N-bytyl iminodiacetic acid salt, N-ethyl,N-(2-aminoethyl)glycine salt and N-methyl,N-(3-aminopropyl)glycine salt.

Now, this invention will be described more specifically below with referance to working examples. It should be noted, however, that this invention is not limited to these working examples.

The numerical values of the conversion of amino alcohol and the selectivity to aminocaroxylic acid salt indicated in the following working examples are results of calculation based on the following formulas.

$$\text{Conversion of amino alcohol (\%)} = \frac{\text{Number of mols of reacted amino alcohol}}{\text{Number of mols of fed amino alcohol}} \times 100$$

$$\text{Selectivity to aminocarboxylic acid salt (\%)} = \frac{\text{Number of mols of formed aminocarboxylic acid salt}}{\text{Number of mols of reacted amino alcohol}} \times 100$$

EXAMPLE 1

An autoclave having an inner volume of 500 ml was charged with 79.3 g of monoethanolamine, 56.0 g of sodium hydroxide, 135.3 g of water and 8.0 g of developed Raney copper. After the interior of the autoclave had been displaced with hydrogen gas three times, the reaction was continued at a temperature of 160° C. under a pressure of 9 kg/cm$^2$.G until generation of hydrogen ceased. The time required for the reaction was 4 hours after the temperature had reached 160° C. After completion of the reaction, the reaction product was sampled and analyzed. By the analysis, the conversion of monoethanolamine was found to be 98.1 mol % and the selectivity to glycine salt to be 97.2 mol %.

EXAMPLE 2

An autoclave having an inner volume of 500 ml was charged with 79.3 g of monoethanolamine, 56.0 g of sodium hydroxide, 135.3 g of water and 8.0 g of metallic copper obtained by thermally decomposing copper formate under a current of hydrogen gas at 200° C. for 3 hours. After the interior of the autoclave had been displaced with hydrogen gas three times, the reaction was continued at a temperature of 160° C. under a pressure of 9 kg/cm$^2$.G until generation of hydrogen ceased. The time required for the reaction was 6 hours after the temperature had reached 160° C. After completion of the reaction, the reaction product was sampled and analyzed. By the analysis, the conversion of monoethanolamine was found to be 97.5 mol % and the selectivity to glycine salt to be 95.1 mol %.

EXAMPLE 3

An autoclave having an inner volume of 500 ml was charged with 79.3 g of monoethanolamine, 78.5 g of potassium hydroxide, 135.3 g of water and 8.0 g of developed Raney copper. After the interior of the autoclave had been displaced with hydrogen gas three times, the reaction was continued at a temperature of 160° C. under a pressure of 9 kg/cm$^2$.G until generation of hydrogen ceased. The time required for the reaction was 4 hours after the temperature had reached 160° C. After completion of the reaction, the reaction product was sampled and analyzed. By the analysis, the conversion of monoethanolamine was found to be 98.2 mol % and the selectivity to glycine salt to be 96.5 mol %.

EXAMPLE 4

An autoclave having an inner volume of 500 ml was charged with of monoethanolamine, 56.0 g of sodium hydroxide, 135.3 g of water and 8.0 g of a catalyst containing copper and zirconium which had been obtained by adding to a solution of 24.8 g of zirconium oxychloride and 4.0 g of copper nitrate in 300 ml of water an aqueous sodium hydroxide solution to cause precipitation of hydroxide, washing the precipitate with water, drying it, heating the dry precipitate in air at 500° C. for 3 hours, and subjecting the resultant oxidized composite to reduction under a current of hydrogen gas at 230° C. for 6 hours. After the interior of the autoclave had been displaced with hydrogen gas three times, the reaction was continued at a temperature of 155° C. under a pressure of 9 kg/cm$^2$.G until generation of hydrogen ceased. The time required for the reaction was 4 hours after the temperature had reached 155° C. After completion of the reaction, the reaction product was sampled and analyzed. By the analysis, the conversion of monoethanolamine was found to be 98.4 mol % and the selectivity to glycine salt to be 98.2 mol %.

EXAMPLE 5

An autoclave having an inner volume of 500 ml was charged with 79.3 g of monoethanolamine, 56 g of sodium hydroxide, 135.3 g of water and 8.0 g of a catalyst having copper deposited on zirconium oxide which had been obtained by impregnating 10 g of zirconium oxide with an aqueous solution containing 4.2 g of copper nitrate, drying the wet oxide, then heating it at 500° C. in air for 3 hours, and subjecting the oxidized composite to reduction under a current of hydrogen gas at 230° C. for 6 hours. After the interior of the autoclave had been displaced with hydrogen gas three times, the reaction was continued at a temperature of 155° C. under a pressure of 9 kg/cm$^2$.G until generation of hydrogen ceased. The time required for the reaction was 4 hours after the temperature had reached 155° C. After completion of the reaction, the reaction product was sampled and analyzed. By the analysis, the conversion of monoethanolamine was found to be 98.2 mol % and the selectivity to glycine salt to be 97.6 mol %.

EXAMPLE 6

To test the catalyst of Example 4 for activity in repeated use, the reaction of Example 4 was performed recurrently by following the same precedure. The time required for the reaction in the 10th cycle was 5 hours after the temperature had reached 155° C. After completion of the reaction, the reaction solution was sampled and analyzed. By the analysis, the conversion of monoethanolamine was found to be 97.6 mol % and the selectivity to glycine salt to be 96.0 mol %.

EXAMPLE 7

An autoclave having an inner volume of 500 ml was charged with 80.0 g of diethanolamine, 64 g of sodium hydroxide, 170.0 g of water and 8.0 g of developed Raney copper. After the interior of the autoclave had been displaced with hydrogen gas three times, the reaction was continued at a temperature of 170° C. under a pressure of 9 kg/cm$^2$.G until generation of hydrogen ceased. The time required for the reaction was 4.5 hours after the temperature had reached 170° C. After completion of the reaction, the reaction product was sampled and analyzed. By the analysis, the conversion of diethanolamine was found to be 97.5 mol %.and the selectivity to iminodiacetic acid salt to be 95.7 mol %.

EXAMPLE 8

An autoclave having an inner volume of 500 ml was charged with 80.0 g of diethanolamine, 64.0 g of sodium hydroxide, 170.0 g of water and 8.0 g of metallic copper obtained by thermally decomposing copper formate under a current of hydrogen gas at 200° C. for 3 hours. After the interior of the autoclave had been displaced with hydrogen gas three times, the reaction was continued at a temperature of 170° C. under a pressure or 9 kg/cm$^2$.G until generation of hydrogen ceased. The time required for the reaction was 6.5 hours after the temperature had reached 170° C. After completion of the reaction, the reaction product was sampled and analyzed. By the analysis, the conversion of diethanolamine was found to be 97.0 mol % and the selectivity to iminodiacetic acid salt to be 94.8 mol %.

EXAMPLE 9

An autoclave having an inner volume of 500 ml was charged with 80.0 g of diethanolamine, 89.8 g of potassium hydroxide, 170.0 g of water and 8.0 g of developed Raney copper. After the interior of the autoclave had been displaced with hydrogen gas three times, the reaction was continued at a temperature of 170° C. under a pressure of 9 kg/cm$^2$.G until generation of hydrogen ceased. The time required for the reaction was 4.3 hours after the temperature had reached 170° C. After completion of the reaction, the reaction product was sampled and analyzed. By the analysis, the conversion of diethanolamine was found to be 98.0 mol % and the selectivity to iminodiacetic acid salt to be 95.4 mol %.

EXAMPLE 10

An autoclave having an inner volume of 500 ml was charged with 80.0 g of diethanolamine, 64.0 g of sodium hydroxide, 170.0 g of water and 8.0 g of a catalyst containing copper and zirconium which had been obtained by adding to a solution of 24.8 g of zirconium oxychloride and 4.0 g of copper nitrate in 300 ml of water an aqueous sodium hydroxide solution to cause precipitation of hydroxide, washing the precipitate with water, drying it, heating the dry precipitate in air at 500° C. for 3 hours, and subjecting the resultant oxidized composite to reduction under a current of hydrogen gas at 230° C. for 6 hours. After the interior of the autoclave had been displaced with hydrogen gas three times, the reaction was continued at a temperature of 160° C. under a pressure of 9 kg/cm$^2$.G until generation of hydrogen ceased. The time required for the reaction was 4.0 hours after the temperature had reached 160° C. After completion of the reaction, the reaction product was sampled and analyzed. By the analysis the conversion of diethanolamine was found to be 97.7 mol % and the selectivity to iminodioacetic acid salt to be 96.0 mol %.

EXAMPLE 11

An autoclave having an inner volume of 500 ml was charged with 80.0 g of diethanolamine, 64.0 g of sodium hydroxide, 170.0 g of water and 8.0 g of a catalyst having copper deposited on zirconium oxide which had been obtained by impregnating 10 g of zirconium oxide with an aqueous solution containing 4.2 g of copper nitrate, drying the wet composite, heating the dried composite in air at 500° C. for 3 hours, and subjecting the oxidized composite to reduction under a current of hydrogen gas at 230° C. for 6 hours. After the interior of the autoclave had been displaced with hydrogen gas three times, the reaction was continued at a temperature of 160° C. under a pressure of 9 kg/cm$^2$.G until generation of hydrogen ceased. The time required for the reaction was 4.2 hours after the temperature had reached 160° C. After completion of the reaction, the reaction product was sampled and analyzed. By the analysis, the conversion of diethanolamine was found to be 97.7 mol % and the selectivity to iminodiacetic acid salt to 95.7 mol %.

EXAMPLE 12

To test the catalyst of Example 10 for activity in repeated use, the reaction of Example 10 was performed recurrently under the same conditions. The time required for the reaction in the 10th cycle was 5.0 hours after the temperature had reached 160° C. After completion of the reaction, the reaction product was sampled and analyzed. By the analysis, the conversion of diethanolamine was found to be 96.2 mol % and the selectivity to iminodiacetic acid salt to be 94.2 mol %.

EXAMPLE 13

An autoclave having an inner volume of 500 ml was charged with 74.5 g of triethanolamine, 63.0 g of sodium hydroxide, 137.5 g of water and 7.5 g of developed Raney copper. After the interior of the autoclave had been displaced with hydrogen gas three times, the reaction was continued at a temperature of 190° C. under a pressure of 9 kg/cm$^2$.G until generation of hydrogen ceased. The time required for the reaction was 7 hours after the temperature had reached 190° C. Ater completion of the reaction, the reaction product was sampled and analyzed. By the analysis, the conversion of triethanolamine was found to be 97.9 mol % and the selectivity to nitrilotriacetic acid salt to be 94.8 mol %.

EXAMPLE 14

An autoclave having an inner volume of 500 ml was charged with 74.5 g of triethanolamine, 63.0 g of sodium hydroxide, 137.5 g of water and 7.5 g of metallic copper obtained by thermally decomposing copper formate under a current of hydrogen gas at 200° C. for 3 hours. After the interior of the autoclave had been displaced with hydrogen gas three times, the reaction was continued at a temperature of 190° C. under a pressure of 9 kg/cm$^2$.G until generation of hydrogen ceased. The time required for the reaction was 9 hours after the temperature had reached 190° C. After completion of the reaction, the reaction product was sampled and analyzed. By the analysis, the conversion of triethanolamine was found to be 97.5 mol % and the selectivity to nitrilotriacetic acid salt to be 91.7 mol %.

EXAMPLE 15

An autoclave having an inner volume of 500 ml was charged with 74.5 g of triethanolamine, 88.4 g of potassium hydroxide, 137.5 g of water and 8.0 g of developed Raney copper. After the interior of the autoclave had been displaced with hydrogen gas three times, the reaction was continued at a temperature of 190° C. under a pressure of 9 kg/cm$^2$.G until generation of hydrogen ceased. The time required for the reaction was 7 hours after the temperature had reached 190° C. After completion of the reaction, the reaction product was sampled and analyzed. By the analysis, the conversion of triethanolamine was found to be 98.2 mol % and the selectivity to nitrilotriacetic acid salt to be 94.9 mol %.

EXAMPLE 16

An autoclave having an inner volume of 500 ml was charged with 74.5 g of triethanolamine, 63.0 g of sodium hydroxide, 137.5 g of water and 7.5 g of a catalyst containing copper and zirconium which had been obtained by adding to a solution of 24.8 g of zirconium oxychloride and 4.0 g of copper nitrate in 300 ml of water an aqueous sodium hydroxide solution to cause precipiration of hydroxide, washing the precipitate with water, drying it, heating dry precipitate in air at 500° C. for 3 hours, and subjecting the resultant oxidized composite to reduction under a current of hydrogen gas at 230° C. for 6 hours. After the interior of the autoclave had been displaced with hydrogen gas three times, the reaction was continued at a temperature of 175° C. under a pressure of 9 kg/cm$^2$.G until generation of hydrogen ceased. The time required for the reaction was 5.5 hours after the temperature had reached 175° C. After completion of the reaction, the reaction product was sampled and analyzed. By the analysis, the conversion of triethanolamine was found to be 98.4 mol % and the selectivity to nitrilotriacetic acid salt to be 95.4 mol %.

EXAMPLE 17

An autoclave having an inner volume of 500 ml was charged with 74.5 g of triethanolamine, 63.0 g of sodium hydroxide, 137.5 g of water and 7.5 g of a catalyst having copper deposited on zirconium oxide which had been obtained by impregnating 10 g of zirconium oxide with an aqueous solution containing 4.2 g of copper nitrate, drying the wet composite, heating the dried composite in air at 500° C. for 3 hours, and subjecting the oxidized composite to reduction under a current of hydrogen gas at 230° C. for 6 hours. After the interior of the autoclave had been displaced with hydrogen gas three times, the reaction was continued at a temperature of 175° C. under a pressure of 9 kg/cm$^2$.G until generation of hydrogen ceased. The time required for the reaction was 6 hours after the temperature had reached 175° C. After completion of the reaction, the reaction product was sampled and analyzed. By the analysis, the conversion of triethanolamine was found to be 98.0 mol % and the selectivity to nitrilotriacetic acid salt to be 94.2 mol %.

EXAMPLE 18

To test the catalyst of Example 16 for activity in repeated use, the reaction of Example 16 was performed recurrently under the same conditions. The time required for the reaction in the 10th cycle was 6.5 hours after the temperature had reached 175° C. After completion of the reaction, the reaction product was sampled and analyzed. By the analysis, the conversion of triethanolamine was found to be 97.3 mol % and the selectivity to nitrilotriacetic acid salt to be 93.5 mol %.

What is claimed is:

1. A method for the manufacture of an aminocarboxylic acid salt by dehydrogenation of an aminoalcohol which comprises contacting an amino alcohol represented by the formula (I):

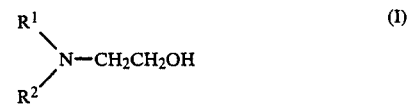

wherein R$^1$ and R$^2$ denote hydrogen, —CH$_2$CH$_2$OH, an alkyl group having 1 to 18 carbon atoms or an aminoalkyl group having 2 or 3 carbon atoms, which may be the same or different, with an alkali or alkaline earth metal hydroxide, water and a catalyst consisting essentially of (1) copper metal or a copper compound and (2) a zirconium compound, in the liquid phase wherein the copper content of said catalyst is between 3 and 50% by weight based on the total amount of copper and zirconium.

2. A method according to claim 1, wherein the amount of said catalyst is 1 to 70% by weight based on the amount of said amino alcohol.

3. A method according to claim 1, wherein the amount of said water exceeds 10% by weight based on amount of said amino alcohol.

4. A method according to claim 1, wherein the amount of said alkali metal hydoxide is not less than 1 equivalent relative to said amino alcohol.

5. A method according to claim 1, wherein the amount of said catalyst is 5 to 30% by weight based on the amount of said amino alcohol.

6. A method according to claim 5, wherein the amount of said water is 50 to 500% by weight based on the amount of said amino alcohol.

7. A method according the claim 1, wherein said alkali metal hydroxide is sodium hydroxide or potassium hydroxide.

8. A method according to claim 1, wherein the reaction temperature is not more than 220° C.

9. A method according to claim 1, wherein the reaction temperature is in the range of 120° to 220° C.

10. A method according to claim 8, wherein the reaction pressure is in the range of 0 to 30 kg/cm$^2$.G.

11. A method according to claim 1, wherein $R^1$ and $R^2$ in said formula I is hydrogen or —CH$_2$CH$_2$OH.

12. A method according to claim 11, wherein said amino alcohol is monoethanolamine and said aminocarboxylic acid salt is glycine salt.

13. A method according to claim 11, wherein said amino alcohol is diethanolamine and said aminocarboxylic acid salt is iminodiacetic acid salt.

14. A method according to claim 11, wherein said amino alcohol is triethanolamine and said aminocarboxylic acid salt is nitrilotriacetic acid salt.

15. A method according to claim 1 wherein said catalyst consists essentially of copper metal and a zirconium compound.

16. A method according to claim 11, wherein said catalyst consists essentially of copper metal and a zirconium compound.

17. A method according to claim 15, wherein said amino alcohol is monoethanolamine or diethanolamine.

* * * * *